United States Patent
Prewett

(10) Patent No.: US 9,814,496 B2
(45) Date of Patent: Nov. 14, 2017

(54) INTERSPINOUS STABILIZATION IMPLANT

(71) Applicant: Hydra Medical, LLC, Bloomfield Hills, MI (US)

(72) Inventor: Ann Prewett, Bloomfield Hills, MI (US)

( * ) Notice: Subject to any disclaimer, the term of this patent is extended or adjusted under 35 U.S.C. 154(b) by 76 days.

(21) Appl. No.: 14/854,631

(22) Filed: Sep. 15, 2015

(65) Prior Publication Data

US 2017/0071638 A1   Mar. 16, 2017

(51) Int. Cl.
*A61B 17/70*   (2006.01)
*A61B 17/00*   (2006.01)

(52) U.S. Cl.
CPC ...... *A61B 17/7067* (2013.01); *A61B 17/7062* (2013.01); *A61B 17/7097* (2013.01); *A61B 2017/00862* (2013.01)

(58) Field of Classification Search
CPC ............ A61B 17/7067; A61B 17/7097; A61B 2017/00862
USPC ....... 606/246, 248, 249, 279, 78; 623/17.11, 623/17.12, 17.16
See application file for complete search history.

(56) References Cited

U.S. PATENT DOCUMENTS

| | | |
|---|---|---|
| 4,107,121 A | 8/1978 | Stoy |
| 4,331,783 A | 5/1982 | Stoy |
| 4,337,327 A | 6/1982 | Stoy |
| 4,369,294 A | 1/1983 | Stoy |
| 4,370,451 A | 1/1983 | Stoy |
| 4,379,874 A | 4/1983 | Stoy |

(Continued)

FOREIGN PATENT DOCUMENTS

| | | |
|---|---|---|
| WO | 2006136938 A1 | 12/2006 |
| WO | 2008068162 A1 | 6/2008 |

OTHER PUBLICATIONS

International Search Report and Written Opinion of the International Searching Authority, PCT/US2009/060896, dated Dec. 18, 2009; 10 pages.

(Continued)

*Primary Examiner* — Pedro Philogene
*Assistant Examiner* — David C Comstock
(74) *Attorney, Agent, or Firm* — Carter, DeLuca, Farrell & Schmidt, LLP

(57) ABSTRACT

A swellable, resilient self-retaining interspinous implant that includes two oppositely disposed retaining members connected by a centrally disposed cross body, the cross body defining a center axis, each retaining member extending in opposite directions relative to each other and perpendicular to the center axis, the implant being dimensioned and configured to fit between two spinous processes of two adjacent vertebrae. In embodiments, the implant has a first configuration of reduced size such that it can be inserted into the patient in a minimally invasive manner. Once inserted to an application point within the patient, the implant expands in size to dynamically maintain the adjacent spinous processes in beneficial alignment. Also provided is a method of making a swellable, resilient interspinous implant as described herein. Also provided is a method of treating a degenerative condition of a spine which includes creating an incision and inserting, through the incision, between two spinous processes of two adjacent vertebrae, a swellable, resilient interspinous implant as described herein.

23 Claims, 6 Drawing Sheets

(56) References Cited

U.S. PATENT DOCUMENTS

| | | |
|---|---|---|
| 4,420,589 A | 12/1983 | Stoy |
| 4,943,618 A | 7/1990 | Stoy et al. |
| 5,252,692 A | 10/1993 | Lovy et al. |
| 5,496,318 A | 3/1996 | Howland et al. |
| 5,571,189 A | 11/1996 | Kuslich |
| 5,609,634 A | 3/1997 | Voydeville |
| 5,645,599 A | 7/1997 | Samani |
| 5,836,948 A | 11/1998 | Zucherman et al. |
| 6,074,390 A | 6/2000 | Zucherman et al. |
| 6,099,531 A | 8/2000 | Bonutti |
| 6,232,406 B1 | 5/2001 | Stoy |
| 6,238,397 B1 | 5/2001 | Zucherman et al. |
| 6,264,695 B1 | 7/2001 | Stoy |
| 6,440,169 B1 | 8/2002 | Elberg et al. |
| 6,626,944 B1 | 9/2003 | Taylor |
| 6,699,247 B2 | 3/2004 | Zucherman et al. |
| 6,726,721 B2 | 4/2004 | Stoy et al. |
| 6,733,534 B2 | 5/2004 | Sherman |
| 6,796,983 B1 | 9/2004 | Zucherman et al. |
| 7,029,473 B2 | 4/2006 | Zucherman et al. |
| 7,101,375 B2 | 9/2006 | Zucherman et al. |
| 7,189,234 B2 | 3/2007 | Zucherman et al. |
| 7,306,628 B2 | 12/2007 | Zucherman et al. |
| 7,361,196 B2 | 4/2008 | Fallin et al. |
| 7,837,688 B2 * | 11/2010 | Boyer, II ............ A61B 17/1671 606/246 |
| 9,131,965 B2 | 9/2015 | Prewett et al. |
| 2004/0167520 A1 | 8/2004 | Zucherman et al. |
| 2005/0245937 A1 | 11/2005 | Winslow |
| 2006/0058790 A1 | 3/2006 | Carl et al. |
| 2006/0084983 A1 | 4/2006 | Kim |
| 2006/0136065 A1 | 6/2006 | Gontarz et al. |
| 2006/0235387 A1 | 10/2006 | Peterman |
| 2006/0241601 A1 | 10/2006 | Trautwein et al. |
| 2006/0247623 A1 | 11/2006 | Anderson et al. |
| 2006/0264938 A1 | 11/2006 | Zucherman et al. |
| 2006/0265066 A1 | 11/2006 | Zucherman et al. |
| 2006/0271049 A1 | 11/2006 | Zucherman et al. |
| 2006/0293662 A1 | 12/2006 | Boyer et al. |
| 2007/0043362 A1 | 2/2007 | Malandain et al. |
| 2007/0135922 A1 | 6/2007 | Trieu |
| 2007/0191956 A1 | 8/2007 | Prewett et al. |
| 2007/0270823 A1 | 11/2007 | Trieu et al. |
| 2007/0276369 A1 | 11/2007 | Allard et al. |
| 2007/0276493 A1 | 11/2007 | Malandain et al. |
| 2008/0249604 A1 | 10/2008 | Donovan et al. |
| 2008/0300686 A1 | 12/2008 | Khoo |
| 2009/0119931 A1 | 5/2009 | Gongola |
| 2009/0297603 A1 | 12/2009 | Joshi |
| 2010/0100183 A1 | 4/2010 | Prewett et al. |

OTHER PUBLICATIONS

International Search Report and Written Opinion of the International Searching Authority, dated Feb. 2, 2017, corresponding to International Application No. PCT/US2016/51624; 14 total pages.

* cited by examiner

INTERSPINOUS STABILIZATION IMPLANT

BACKGROUND

1. Technical Field

Dynamic stabilization of the spine.

2. Description of Related Art

Physical discomfort from degenerative conditions of the spine such as disc disease, spinal stenosis, and spondylolisthesis affects a large segment of the population. Symptoms are related to compression of spinal nerves or nerve roots and may include intermittent neurogenic claudication, pain in back or legs, numbness, weakness and loss of balance. Conservative treatment may include rest, physical therapy, bracing, anti-inflammatory medications, analgesics, local anesthetic blocks and epidural steroid injections.

Treatment by spinal fusion is frequently offered to patients who suffer from these conditions. However, fused vertebrae have been associated with loss of mobility and deterioration of adjacent discal architecture due to increased strain and forces at such discs. Dynamic spinal stabililization of the spine is a treatment modality intended to overcome such deficiencies. Dynamic stabilization allows adjacent vertebrae to be stabilized through the use of, e.g., articulating structures, compressible structures and the like, to allow relative movement of adjacent vertebrae which are supported by such structures. In this manner, the aforementioned disadvantages of rigid fusion are avoided.

Surgical decompression with or without fusion is a standard surgical treatment for patients with moderate to severe lumbar spinal stenosis. Cervical, thoracic, and/or lumbar interspinous process decompression (IPD), also known as interspinous distraction or posterior spinal distraction, is a form of dynamic stabilization that has been proposed as a minimally invasive alternative to laminectomy and fusion. In IPD an interspinous distraction implant is inserted between the spinous processes through a small (e.g., 4-8 cm) incision. The implant is intended to restrict painful motion while enabling otherwise normal motion. The implant forms a wedge that enlarges the neural foramen, decompresses the cauda equina and acts as a spacer between the spinous processes to maintain the flexion of the spinal interspace. This reduces pressure on the exiting nerves and allows for relief from sciatica and oftentimes back pain as well. Due to the off-loading of the posterior spinal disc, small tears and herniations may improve as well.

Many implants designed for dynamic stabilization are inserted using open procedures. Minimally invasive surgical techniques are used to minimize trauma to a patient by reducing the size of a surgical wound. A percutaneously inserted interspinous spacer can optimize patient outcome by further minimizing the surgical incision and accompanying tissue damage. US Patent Appln. Pub. No. 2010/0100183, filed Sep. 15, 2015, incorporated herein by reference in its entirety, is directed to a swellable interspinous stabilization implant. In embodiments, the implant has a first configuration of reduced size such that it can be inserted into a patient in a minimally invasive manner. Once inserted to an application point within the patient, the implant expands in size to dynamically maintain the adjacent spinous processes in beneficial alignment.

There is continuing need for improved methods and devices for stabilizing compromised spinal architecture.

SUMMARY

A swellable, resilient self-retaining interspinous implant is provided that includes two oppositely disposed retaining members connected by a centrally disposed cross body, the cross body defining a center axis, each retaining member extending in opposite directions with respect to each other and asymmetrically with respect to the center axis, the implant being dimensioned and configured to fit between two spinous processes of two adjacent vertebrae. The implant acts to stabilize adjacent vertebrae by engaging the spinous processes of adjacent vertebrae and removing slack from the system. In embodiments, the cross body has a flat superior surface dimensioned and configured to receive a superior process of a superior vertebrae. In embodiments, the cross body has a flat inferior surface dimensioned and configured to receive a inferior process of a inferior vertebrae. In embodiments, the implant has a first configuration of reduced size such that it can be inserted into the patient in a minimally invasive manner. In embodiments, the reduced configuration is a Z-shape. In embodiments, the reduced configuration is a parallelogram shape. In embodiments, the reduced configuration is a cigar shape. In embodiments, at least one of the retaining members contains a collapsible aperture. In embodiments, the collapsible aperture is triangular when not collapsed and crescent shaped when collapsed. Once inserted to an application point within the patient, the implant expands in size to dynamically maintain the adjacent spinous processes in beneficial alignment. In embodiments, the implant is made of a swellable polymeric medium which may be a fluid absorbing polymer, e.g., a hydrogel. In embodiments, the fluid absorbing polymer contains a plasticizer. The swellable polymeric medium may also be a substantially non-fluid absorbing elastic polymer. In embodiments, the implant is capable of expanding from a compact, substantially dehydrated configuration to an expanded hydrated configuration. In embodiments, the implant is configured to transform from a first configuration to a second configuration, the first configuration having a smaller cross-section than the second configuration. In embodiments, the implant is capable of undergoing anisotropic expansion from the first configuration to the second configuration. In embodiments, the implant is capable of undergoing isotropic expansion from the first configuration to the second configuration.

In embodiments, the implant includes an interiorly disposed support member. In embodiments, at least a portion of the interiorly disposed support member extends beyond the periphery of the implant. In embodiments the support member is made of flexible fibers. The flexible fibers may be made, e.g., from natural or synthetic polymers or metal. In embodiments, the support member is fabric selected from the group consisting of mesh, woven fabric and nonwoven fabric made of flexible fibers. In embodiments, the support member is a braided three-dimensional support member made of flexible fibers. In embodiments, the interstices of the braided three-dimensional support member are filled with the polymeric medium. In embodiments, the support member is a flexible foil made from metal or a polymer. In embodiments, at least a portion of the implant includes a wear reducing surface adapted and configured to contact bone.

In embodiments, a radiopaque material may be included in or around the implant. In embodiments, the radiopaque material is located in at least a portion of at least one retaining member. In embodiments, the retaining member containing the radiopaque material has an end portion which contains the radiopaque material, wherein upon expansion of the implant from the first configuration to the second configuration, the end portion which contains the radiopaque material defines an first position in the first configuration and second positon position in the second configuration, the second position serving as an indication that the implant is in the second configuration.

Also provided is a method of making a swellable, resilient interspinous implant which includes providing a mold defining a cavity dimensioned and configured to approximate at least a portion of the space between two spinous processes of two adjacent vertebrae, the cavity defining first and second end portions and a center portion connecting the first and second end portions, providing a liquid polymer, filling the mold with the liquid polymer and solidifying the liquid polymer to form a swellable, resilient interspinous implant that includes two oppositely disposed retaining members connected by a centrally disposed cross body, the cross body defining a center axis, each retaining member extending in opposite directions with respect to each other and asymmetrically with respect to the center axis, the implant being dimensioned and configured to fit between two spinous processes of two adjacent vertebrae. In embodiments, the mold cavity defines first and second end portions extending in opposite directions. In embodiments, the cavity is Z-shaped. In embodiments, the cavity is S-shaped. In embodiments, the method further includes providing a support member, positioning the support member in said mold such that the liquid polymer can at least partially cover the support member, and solidifying the liquid polymer. In embodiments, the support member is a braided three-dimensional member configured and dimensioned to have a shape consistent with the mold cavity. In embodiments the liquid polymer is a fluid absorbing polymer. The fluid absorbing polymer can be a hydrogel. In embodiments, a support member, e.g., a braided three-dimensional support member is placed within a mold cavity which has dimensions greater than the braided three-dimensional support member to allow the liquid fluid absorbing polymer to be absorbed into and saturate the braided three-dimensional support member and to encapsulate the braided three-dimensional support member with a layer of fluid absorbing polymer. In embodiments, the interspinous implant is dehydrated to reduce the dimensions of the implant.

Also provided is a method of treating a degenerative condition of a spine which includes creating an incision and inserting, through the incision, between two spinous processes of two adjacent vertebrae, a swellable, resilient interspinous implant that includes two oppositely disposed retaining members connected by a centrally disposed cross body, the cross body defining a center axis, each retaining member extending in opposite directions with respect to each other and asymmetrically with respect to the center axis, the implant being dimensioned and configured to fit between two spinous processes of two adjacent vertebrae, wherein the implant is made of a fluid absorbing polymer which expands from a substantially dehydrated compact first configuration to an expanded second configuration upon absorption of fluid. In embodiments, the interspinous implant is secured to a guide wire and implanted percutaneously. In embodiments, the interspinous implant includes an internal shaft coaxial with the center axis of the implant for receiving the guide wire. In embodiments, the implant has a first configuration of reduced size such that it can be inserted into the patient in a minimally invasive manner. In embodiments, the implant is configured to transform from a first configuration to a second configuration, the first configuration having a smaller cross-section than the second configuration. Once inserted to an application point within the patient, the implant expands in size to dynamically maintain the adjacent spinous processes in beneficial alignment.

DETAILED DESCRIPTION OF PREFERRED EMBODIMENTS

Figure 1:
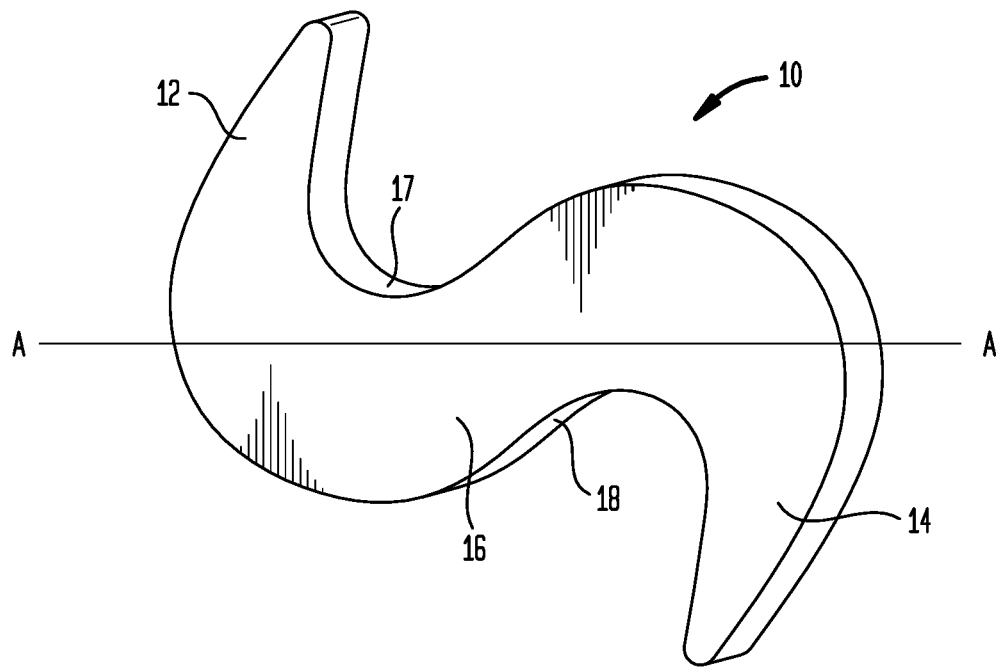
FIG. 1 is a dimensional view of an embodiment of an interspinous implant in an expanded state.

A swellable, resilient, interspinous implant according to the present disclosure is uniquely suited for minimally invasive interspinous implantation by virtue of its ability to achieve an optimum implantable substantially reduced configuration and further ability to expand anisotropically or isotropically to an expanded configuration which is adapted and configured to fit between, and secure, two spinous processes of two adjacent vertebrae and buttress the space between the two adjacent vertebrae. The principles described herein provide an interspinous implant which, in the reduced or compacted configuration, has a suitably narrow cross-section and is elongate in the longitudinal direction along a center axis. See, e.g., FIGS. 3 through 5, 7, 12, 13. "Reduced", "compact" and "compacted" are used interchangeably herein and are also referred to as a first configuration. The reduced configuration fits through a minimally invasive incision as a result of its dimensions and stable structure. After implantation, the interspinous implant can expand anisotropically or isotropically from the reduced configuration into an expanded configuration having an S-shape or a Z-shape which fills at least a majority of the interspinous space between two vertebrae as it expands and also secures itself in place (i.e., self-retaining) by frictionally engaging the vertebral processes.

In embodiments, the unconstricted volume of the interspinous implant, when expanded (also referred to herein as the second configuration), is slightly greater than the interspinous space between two adjacent vertebrae when the spine is in a neutral position such that, in situ, the implant is slightly compressed in a cross body region of the implant when the spine is in the neutral position. In this manner, the interspinous implant exerts positive pressure against the vertebrae to alleviate compression during extension, effectively acting as an extension stop while allowing freedom of spinal flexion. The cross body region also acts as a shock absorber, thereby attenuating compressive forces acting on the spinal column. In addition, maintaining pressure within the interspinous space helps secure the interspinous implant in place by virtue of the friction created thereby.

The shape and volume of the implant in the compacted state is engineered, in accordance with the present disclosure, in order for the implant to function in the compacted insertion state and achieve an expanded state thus providing the following: 1) suitable expansion of the interspinous space, 2) adequate support on the superior and inferior aspects of the cross body, 3) length sufficient to span the interspinous space, and 4) retaining members to control migration of the implant when in the compacted state and during the functional life of the expanded implant.

An aspect of a reducible spinous implant that permits these four conditions to be met is the presence of two retaining members, one disposed superiorly and the other disposed inferiorly with respect to the spinous processes superior and inferior aspects. The retaining members hydrate and swell and resist migration in torsion as one or the other of the retaining members is engaged during motion and hits the facet. The retaining members also frictionally engage the lateral aspect of the spine on either side of the implant thereby resisting lateral migration. In embodiments, the retaining members can be compacted anisotropically to form a reduced profile as compared to an expanded configuration that reduces the insertion dimensions of the implant and allows for a reduced profile percutaneous implantation. In embodiments, the retaining members can be compacted isotropically to form a reduced profile as compared to an expanded configuration that reduces the insertion dimensions of the implant and allows for a reduced profile percutaneous implantation.

In embodiments, the interspinous implant has a first retaining member, an oppositely disposed second retaining member and an interconnecting cross body. As mentioned above, in embodiments, the interspinous implant has an S-shape when, e.g., it is in the expanded configuration. The cross body is dimensioned and configured to be disposed between the bone architecture defining the interspinous space between two adjacent vertebrae and to exert positive pressure against extension. The oppositely disposed first and second end retainer portions are dimensioned and configured to engage the spinous processes of adjacent vertebrae at their respective outer sagittal faces and anchor the central portion of the interspinous implant in place against the lamina and respective vertebral bodies. The inward facing surfaces of the two respective retaining members frictionally engage the outer sagittal faces of the respective spinous processes. In embodiments, the ends of the retaining members are tapered. In embodiments, the S-shape incorporates a curvilinear cross body. See, e.g., FIG. 1. In embodiments, the S-shape incorporates a linear cross body. See, e.g., FIG. 2.

Figure 2:
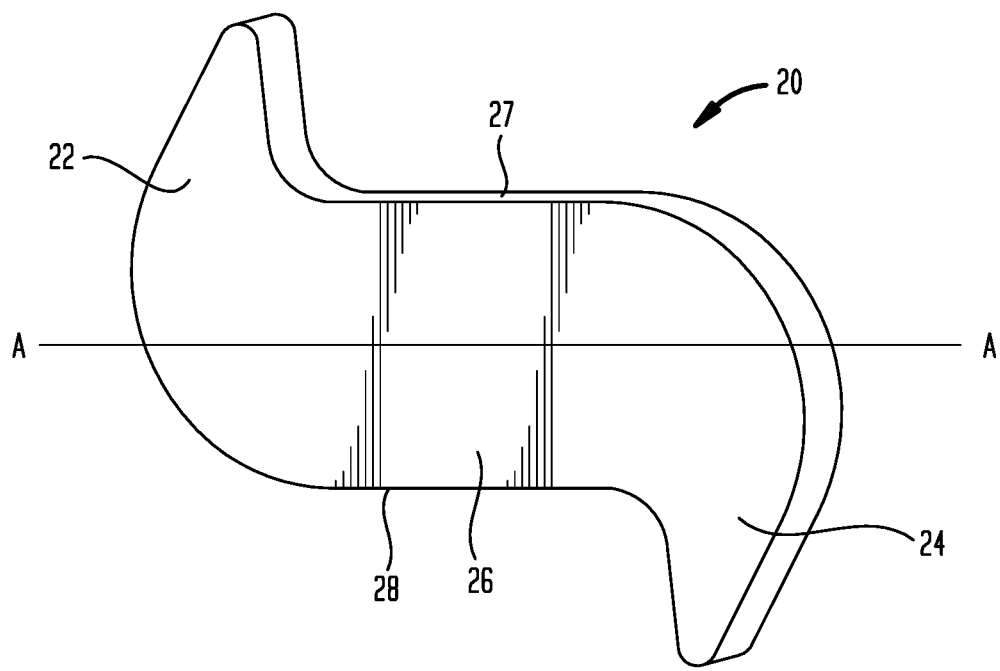
FIG. 2 is a dimensional view of an embodiment of an interspinous implant in an expanded state.

An example of an S-shape interspinous implant 10 is shown in FIG. 1. The interspinous implant 10 has a first retaining member 12, an oppositely disposed second retaining member 14 and curvilinear cross body 16. A flat superior surface 17 is configured to engage the bottom of a superior spinous process. A flat inferior surface 17 is configured to engage the top of an inferior spinous process. FIG. 2 depicts another example of an S-shape interspinous implant 20. The interspinous implant 20 has a first retaining member 22, an oppositely disposed second retaining member 24 and linear cross body 26. A flat superior surface 27 is configured to engage the bottom of a superior spinous process. A flat inferior surface 27 is configured to engage the top of an inferior spinous process.

In embodiments, the cross body defines a longitudinal center axis depicted, e.g., as line A-A in FIGS. 1 and 2, and the first retaining member 12, 22 and the second retaining member 14, 24 extend in opposite directions relative to each other and asymmetrically with respect to the center axis A-A. As shown, one retaining member 12, 22 extends upwardly from the center axis and the other respective retaining member 14, 24 extends downwardly from the center axis.

Figure 6:
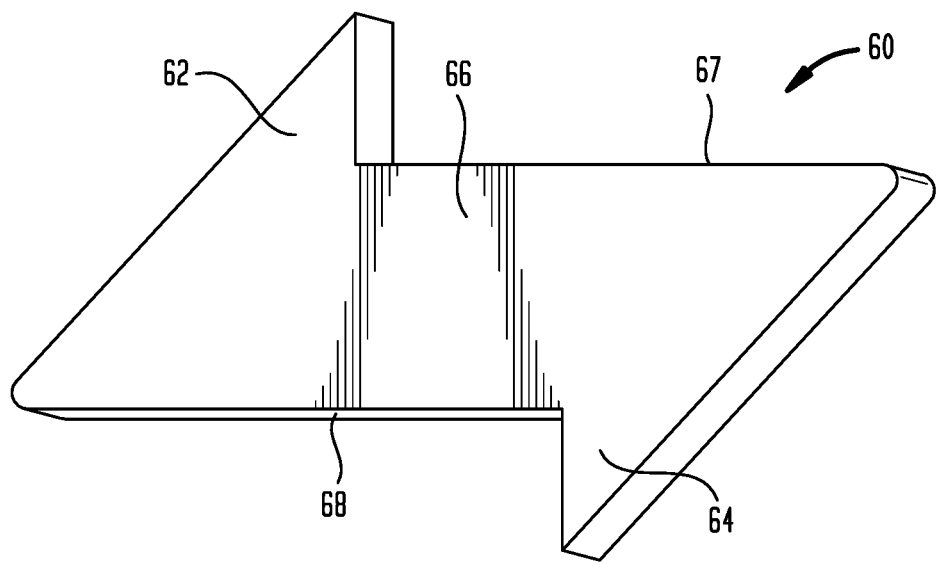
FIG. 6 is a dimensional view of an embodiment of an interspinous implant in an expanded state having a Z-shape configuration.

An example of an interspinous implant 60 having a Z-shape in the expanded configuration is shown in FIG. 6. The interspinous implant 60 has a first retaining member 62, an oppositely disposed second retaining member 64 and linear cross body 66. A flat superior surface 67 is configured to engage the bottom of a superior spinous process. A flat inferior surface 68 is configured to engage the top of an inferior spinous process.

Figure 3:
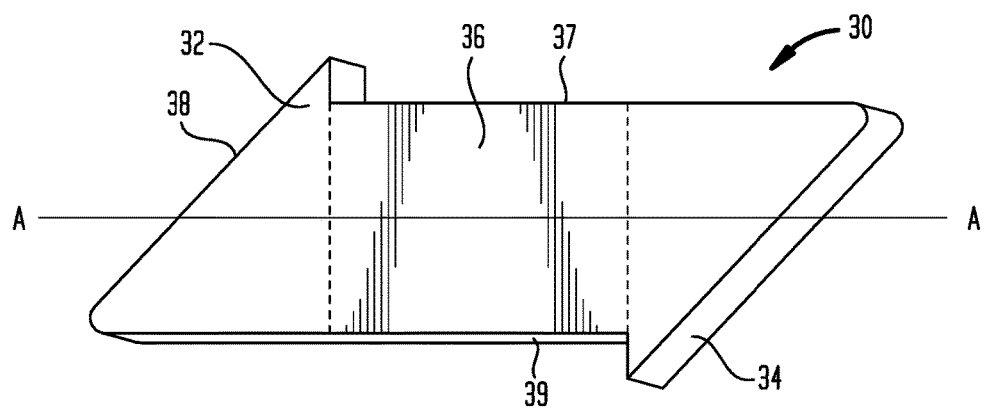
FIG. 3 is a dimensional view of an embodiment of an interspinous implant in a compacted state having a Z-shape configuration.

In embodiments, e.g., shown in FIG. 3, the cross body 36 shown between dashed lines and defines a substantially rectangular cross-section which provides substantially flat superior surface 36 for contacting the process of a superior vertebrae and a substantially flat inferior surface 39 for contacting the process of an inferior vertebrae. Substantially flat surfaces are also illustrated in FIG. 1 as 17, 18, in FIG. 2 as 27, 28, and in FIG. 6 as 67, 68. A substantially flat superior and/or inferior surface resting against the spinous processes assists in stabilizing the implant and inhibits rotation and/or movement of the implant as it sits between the spinous processes of adjacent vertebrae. The superior surface or inferior surface resting against the spinous process should be sufficiently wide, e.g., ranging about 6 mm to about 18 mm, e.g., about 8 mm to about 15 mm, in order to support the load generated by vertebral movement. The length of the cross body located between the spinous processes should be substantially equivalent to the length of the interspinous space which can typically range from about 6 mm to about 18 mm, e.g., 8 mm to about 15 mm, e.g., about 10 mm to about 12 mm. The height of the implant may be determined by the desired extraction height, typically about 8 mm to about 16 mm.

Figure 8:
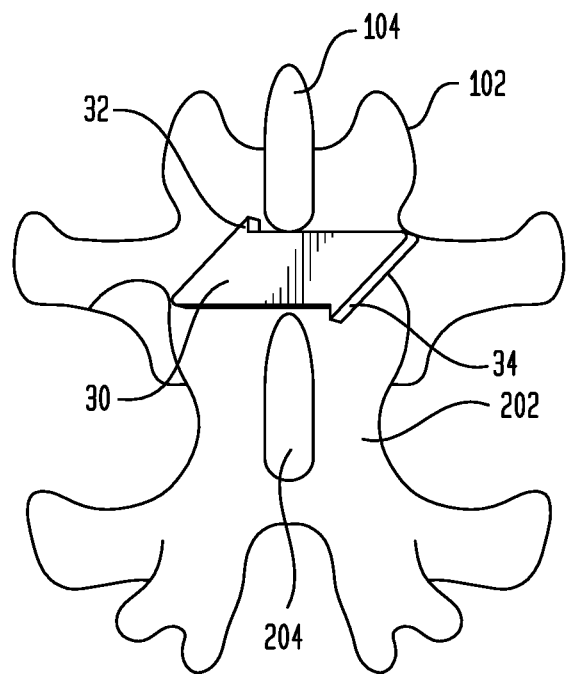
FIG. 8 is a posterior view of an embodiment of an interspinous implant in a compacted state situated between two spinous processes.

In embodiments, the interspinous implant is in a compacted state, i.e., the first configuration. In embodiments, the first configuration defines a Z-shape as seen, e.g., in FIG. 3. Interspinous implant 30 includes a first retaining member 32, a second retaining member 34 and a cross body 36. In embodiments, the cross body defines a longitudinal center axis depicted, e.g., as line A-A in FIG. 3, and the first retaining member 32 and the second retaining member 34 extend in opposite directions relative to each other and asymmetrically with respect to the center axis A-A, i.e., as shown, first retaining member 32 extends upwardly with respect to the center axis and second retaining member 34 extends downwardly with respect to the center axis. Sloped region 38 presents a surface that facilitates percutaneous insertion of the implant 30 through an incision and across the vertebral space between adjacent processes. In embodiments, the sloped surface and first retaining member performs a barb function, e.g., when the implant 30 passes through the vertebral space and the retaining member 32 engages an outer sagittal face of the superior process. See, e.g., FIG. 8. Retaining member 34 engages an outer sagittal face of the inferior process as shown, e.g., in FIG. 8. Both retaining members 32 and 34 keep the compacted implant 30 from sliding out of the vertebral space. The overall configuration of the implant 30, 30', 40 and 50 allows the implant to be inserted without regard to which end is leading. In embodiments, when in the compacted configuration, the ratio of the height of the portion of the implant including the retaining member to the height of the cross body can be, e.g., 3/2. For example, when in the compact configuration, the height of the retaining member portion of the implant may be about 12 mm and the height of the cross body may be about 8 mm. In embodiments, the height of the retaining member portion of the implant may be about 8 mm and the height of the cross body may also be about 8 mm. It should be understood that the ratio and heights provided herein are merely exemplary and that the relative heights of the retainer member portion and the cross body portion may be varied by those skilled in the art to meet varied dimensions within the interspinous space as needed. In embodiments, when seated between adjacent vertebrae the implant 30 expands to either the S-shape configuration shown in FIG. 1, the S-shape configuration shown in FIG. 2 or the Z-shape configuration shown in FIG. 6.

Figure 4:
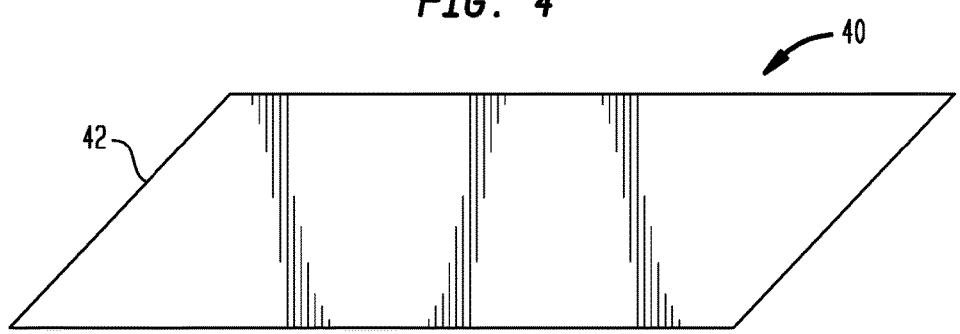
FIG. 4 is a front view of an embodiment of an interspinous implant in a compacted state having a parallelogram shape.

In embodiments, the first configuration of the spinal implant 40 defines a parallelogram as shown, e.g., in FIG. 4. The slope region 42 presents a surface that facilitates percutaneous insertion of the implant 40 through an incision and across the vertebral space between adjacent processes. When seated between adjacent vertebrae the implant 40 expands anisotropically to either the S-shape configuration shown in FIG. 1, the S-shape configuration shown in FIG. 2 or the Z-shape configuration shown in FIG. 6.

Figure 5:
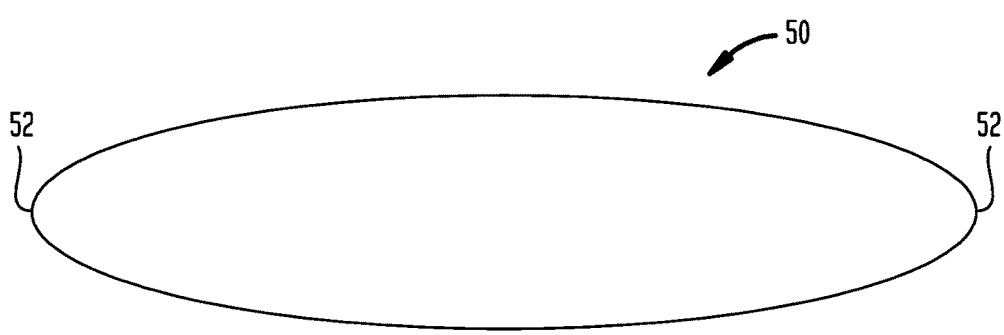
FIG. 5 is a front view of an embodiment of an interspinous implant in a compacted state having a cigar shape.

In embodiments, the first configuration of the spinal implant 50 defines a cigar shape as shown, e.g., in FIG. 5. The tapered ends 52 present a surface that facilitates percutaneous insertion of the implant 50 through an incision and across the vertebral space between adjacent processes. When seated between adjacent vertebrae the implant 50 expands anisotropically to either the S-shape configuration shown in FIG. 1, the S-shape configuration shown in FIG. 2 or the Z-shape configuration shown in FIG. 6.

Figure 7:
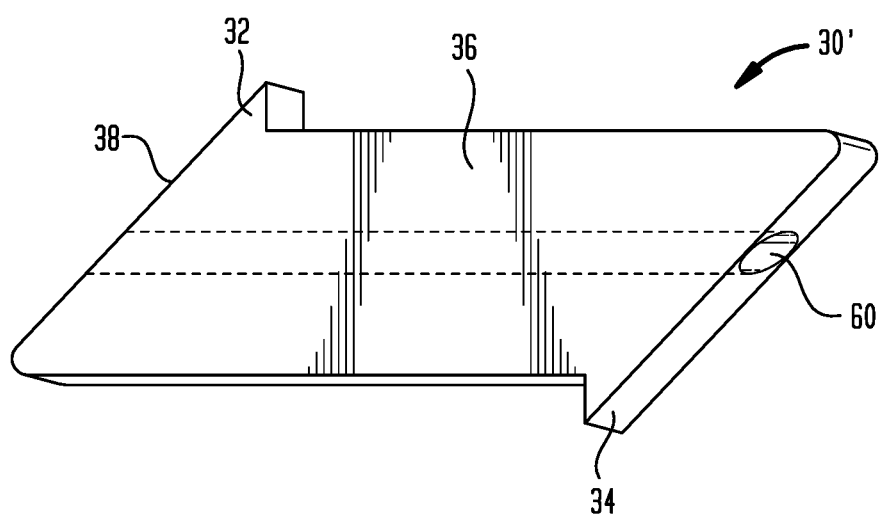
FIG. 7 is a dimensional view of an embodiment of an interspinous implant in a compacted state having a Z-shape configuration and a centrally disposed conduit.

In embodiments, a compacted interspinous implant 30' includes an internal conduit 60 for receiving a guide wire as shown, e.g., in FIG. 7. The conduit is coaxial with the longitudinal center axis of the implant 30' and dimensioned to receive a guide wire (not shown). As described more fully below, a guide wire may be used to position a swellable interspinous implant between the spinous processes.

An interspinous implant herein is swellable and resilient which permits the implant to be inserted to the point of application in its reduced configuration through a minimally invasive incision, e.g., about 4-10 mm. Once in place, the implant expands, depending on the method of compaction as discussed herein, either isotropically or anistropically, to its expanded configuration which, due to the swellability and resiliency of the polymer, at least partially conforms to the topography of the interspinous space between adjacent vertebrae. As a result, an interspinous implant according to the present disclosure provides a shock absorbing cushiony custom fit for the implant that, along with the frictional engagement discussed above, avoids the need for rigid, traumatic attachments to the vertebral bone. In addition, the supraspinous ligament is maintained and assists in holding the implant in place. No laminotomy, laminectomy or foraminotomy is necessary.

Interspinous implants herein made of a swellable fluid absorbing polymer allow reduction of the insertion size of the implants in general and of particular components of the implants, e.g., the retaining members, by removal of fluid contained in the implant. When the fluid absorbing polymer is a hydrogel, dehydration is used to reduce the volume of the implant. This allows for the insertion of the implant in a size that is equal to or less than the size of the dilated interspinous space allowing for a minimally invasive surgical procedure.

In the case of hydrogels, the insertion volume is limited to the extent that the implant can be dehydrated. However, since the implant must have specific mechanical properties, the water content of the implant must be controlled in order to ensure that the swollen implant will exert sufficient pressure to expand the spinous processes. When the water content of the implant exceeds about 60 to about 70% by weight, the implant will not have sufficient stiffness to distract the spinous processes. Therefore, as the water content defines the ratio of hydrated to dehydrated state (the higher the water content, the higher this ratio), the ability to which the insertion shape of the implant can be minimized is dependent on the hydrated volume of the implant. When water content of the hydrated hydrogel is fixed, the volume of the dehydrated material will be a constant (to the extent the shape is identical). In embodiments, the water content of the hydrated implant can range from about 30% to about 70% by weight, e.g., about 40% to about 60% by weight, e.g., about 50%.

Fluid absorbing polymers are well-suited for manufacturing a swellable, resilient interspinous implant in accordance with the present disclosure. Suitable fluid absorbing polymers include synthetic polymers such as poly(ethylene glycol), poly(ethylene oxide), partially or fully hydrolyzed poly(vinyl alcohol), polyvinylpyrrolidone, copolymers of polyacrylic acid and polyvinylpyrrolidone, poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof. Examples of materials that can be used to form a hydrogel include modified alginates. Alginate is a carbohydrate polymer isolated from seaweed, which can be crosslinked to form a hydrogel by exposure to a divalent cation such as calcium. Alginate is ionically crosslinked in the presence of divalent cations, in water, at room temperature, to form a hydrogel matrix. Modified alginate derivatives may be synthesized which have an improved ability to form hydrogels.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Other polymeric hydrogel precursors include polyethylene oxide-polypropylene glycol block copolymers such as Pluronics™ or Tetronics™, which may be crosslinked by hydrogen bonding and/or by a temperature change. Other materials which may be utilized include proteins such as fibrin, collagen and gelatin. Polymer mixtures also may be utilized. For example, a mixture of polyethylene oxide and polyacrylic acid or other combinations such as polyacrylic acid-polyvinylpyrrolidone copolymers which gel by hydrogen bonding upon mixing may be utilized. In embodiments, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Water soluble polymers with charged side groups may be crosslinked by reacting the polymer with an aqueous solution containing ions of the opposite charge, either cations if the polymer has acidic side groups or anions if the polymer has basic side groups. Examples of cations for cross-linking of the polymers with acidic side groups to form a hydrogel are monovalent cations such as sodium, divalent cations such as calcium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin. The polymers can be covalently crosslinked as well through the addition of ethylene diamine, NBS or a host of crosslinking agents routinely to react with amino, nitrile, urethane and carboxylic functional groups found on the polymer chain.

Suitable ionically crosslinkable groups include phenols, amines, imines, amides, carboxylic acids, sulfonic acids and phosphate groups. Aliphatic hydroxy groups are not considered to be reactive groups for the chemistry disclosed herein. Negatively charged groups, such as carboxylate, sulfonate and phosphate ions, can be crosslinked with cations such as calcium ions. The crosslinking of alginate with calcium ions is an example of this type of ionic crosslinking. Positively charged groups, such as ammonium ions, can be crosslinked with negatively charged ions such as carboxylate, sulfonate and phosphate ions. Preferably, the negatively charged ions contain more than one carboxylate, sulfonate or phosphate group.

Anions for cross-linking of the polymers to form a hydrogel are monovalent, divalent or trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

In embodiments, the interspinous implant is made of a hydrogel. Prior to coagulation, the liquid form of a suitable hydrogel is used to form the expanded configuration as it would be in the hydrated state. The hydrogel is then coagulated to form the implant in an expanded configuration. The interspinous implant may then be dehydrated to a xerogel state which reduces the volume of the implant to the reduced configuration. Many hydrogel polymers behave in a similar manner, which is to say they can be deformed, frozen into a deformed shape and they can maintain that shape indefinitely or until, e.g., a temperature change causes the polymer to "relax" into the shape originally held prior to freezing. This property is often referred to as shape memory or frozen deformation by those skilled in the art.

The temperature at which frozen deformation occurs is referred to as the glass transition temperature or $T_g$. At $T_g$ several polymer properties such as density, entropy and elasticity may sharply change. Many polymers can be mixed with agents that can have a drastic effect on a polymer $T_g$. Polymers which absorb fluid are of particular interest and water is the preferred $T_g$ altering agent. Hydrogels which contain less than about five percent water may be considered dehydrated or xerogels. The $T_g$ of a xerogel will change as it absorbs fluids containing water. Once the $T_g$ becomes lower than ambient the now partially hydrated hydrogel becomes pliant and may be elastically deformed. If the polymer is held in a state of elastic deformation while the $T_g$ is raised above ambient the polymer will maintain the deformed state indefinitely. This can be accomplished by either lowering the ambient temperature (freezing) or by returning the polymer to its xerogel state thus raising the $T_g$.

Using this method, hydrogel articles may be produced with vastly differing substantially dehydrated shapes compared to hydrated shapes. This is especially useful in cases such as medical implants where, in delivering a prosthesis into the human body, every care should be taken to reduce trauma to the patient. An implant which has an S-shape, for instance, is re-shaped into Z-shape, a parallelogram shape, or a cigar shape as shown in FIGS. 3-5, 7, 8, 12, 13 in order to facilitate minimally invasive implantation. Alternatively, a portion of the implant can be compressed as compared to another portion of the implant. As discussed above, the retaining members may be compressed more than the cross body. See, e.g., FIGS. 4, 5, 7, 12, 13. Indeed, various frozen shapes may be utilized to facilitate implantation and situation of the implant. Once the implant is indwelling and has absorbed water containing liquids it will substantially return to the expanded S-shape and maintain that shape indefinitely. In embodiments, the implant will substantially return to a Z-shape configuration.

In embodiments, the degree of expansion can be manipulated in hydrogels containing acidic side groups such as acrylic acid. For example, the hydrogel polymer can be washed with an acidic solution to create a neutral to slightly acidic pH. Upon exposure to bodily fluids, the polymer will deprotonate with a pH established by that of the surrounding bodily fluids which is between approximately pH of 7 to 7.4. The acid polymer, which acts as a buffer, will lose protons to the surrounding body fluid/tissue and, in so doing, produces negatively charged ions which will increase the water content of the implant in order to reduce repulsion of the negative charges of the side chains. This in turn will increase the swelling ratio of dry to hydrated polymer.

In embodiments, the compacted implant is plasticized using a plasticizer such as glycerol, polyethylene glycol, Tweens such as Tween 20, Tween 80, polyethylene oxide polymers or water such that between about 15 to about 20 percent of the implant by weight consists of plasticization fluid, e.g., a combination of water and glycerol or other suitable plasticizer. In this manner, the implant will have some flexibility and can be bent at slight angles without breaking, e.g., between about 3 degrees to about 30 degrees, while still retaining sufficient rigidity to allow the implant to be inserted through a vertebral space without detrimental deformation. Detrimental deformation occurs when the implant cannot pass through obstructions in the vertebral space without deforming to such an extent that the implant collapses upon itself and/or bends to such an extent that insertion is difficult or impossible. In embodiments, the modulus of elasticity of the implant can range from about 2.5 MPa to about 5.0 MPa.

Figure 12:
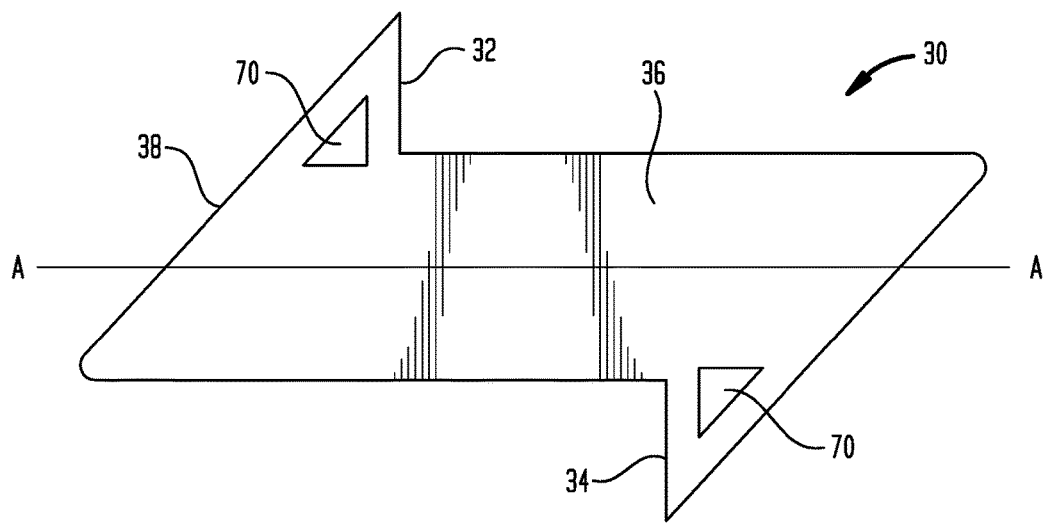
FIG. 12 is a front view of an embodiment of an interspinous implant having a triangular collapsible aperture in each retaining member.
Figure 13:
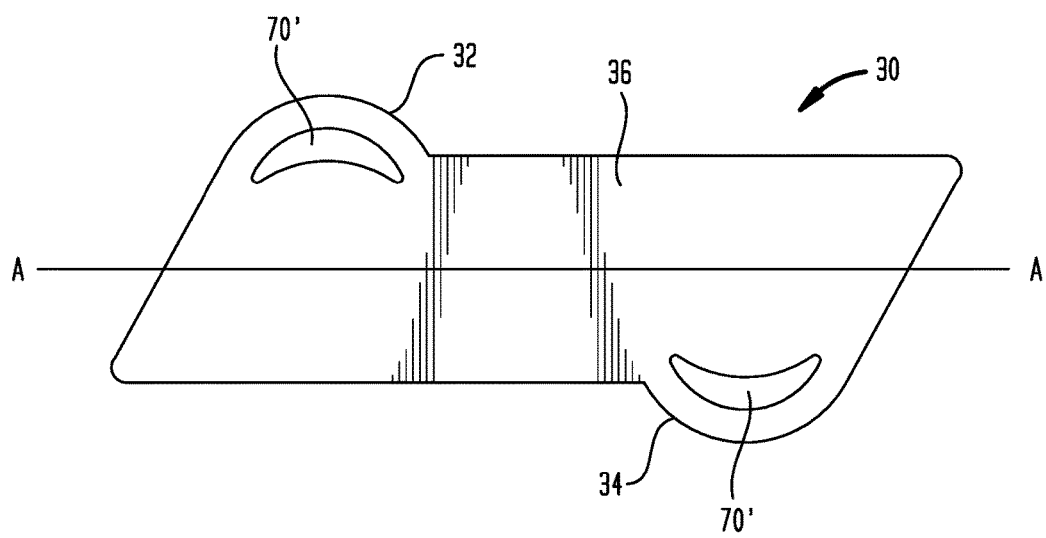
FIG. 13 is a front view of the interspinous implant shown in FIG. 12 wherein each retaining member is at least partially collapsed, thereby reconfiguring the collapsible aperture into a crescent shape.

In embodiments, at least one of the retaining members contains a collapsible aperture. In FIGS. 12 and 13 the implant 30 is shown in a compact configuration. In FIG. 12, each retaining member 32 and 34 contains a collapsible aperture 70. In FIG. 12, the apertures 70 are shown as a triangular shape. Incorporation of a plasticizer provides sufficient flexibility for the collapsible apertures 70 to collapse and assume a collapsed configuration shown, e.g., in FIG. 13 as a crescent shape 70'. It should be understood that those skilled in the art can envision numerous geometric shapes for the aperture such as ellipsoid, e.g., circular, oval, etc., polygonal (square, pentagonal, hexagonal, etc.), star, asterisk, or irregular shapes such as kidney shapes.

In embodiments, when in the compacted configuration and the collapsible aperture is collapsed, the ratio of the height of the portion of the implant including the retaining member to the height of the cross body can be, e.g., about 5/4. For example, when in the compact configuration, the height of the retaining member portion of the implant may be about 10 mm and the height of the cross body may be about 8 mm. In embodiments, the height of the retaining member portion of the implant may be about 8 mm and the height of the cross body may be about 8 mm. It should be understood that the ratio and heights provided herein are merely exemplary and that the relative heights of the retainer member portion and the cross body portion may be varied by those skilled in the art to meet varied dimensions within the interspinous space as needed.

Incorporation of at least one collapsible aperture allows the retaining members to partially collapse even in the dry state with sufficient plasticizer, thus reducing mass and the cross sectional area of the implant which is advantageous in a minimally invasive setting. Accordingly, the aperture, and consequently, the retaining member, can collapse more efficiently than a solid polymeric retaining member can, even in the plasticized dry state. Since the retaining ends are not required to support weight during insertion, they can be collapsed prior to insertion either by insertion into a cannula or other insertion instrument that applies pressure. In embodiments, the retaining members containing uncollapsed collapsible apertures will partially collapse due to environmental resistance or pressure upon or during insertion. For example, as the implant is inserted into and forced across the interspinous space, the retaining member with the collapsible aperture will collapse as the implant is meets resistance, thus reducing the profile of the implant to facilitate insertion and obstruction avoidance. In addition, the implant may be more biocompatible because the retaining members will not exert as much pressure on the soft tissue surrounding them on sides of the spinous processes.

As used herein, "substantially" is intended to mean any of "approximately", "nearly" or "precisely." It should be understood that unless otherwise indicated, absolute terms should be considered as being modified by "substantially." For example, "perpendicular", as used herein encompasses "substantially perpendicular", "dehydrated" encompasses "substantially dehydrated", "rectangular" encompasses "substantially rectangular", "flat" encompasses "substantially flat", "S-shape" encompasses "substantially S-shaped", "Z-shape" encompasses "substantially Z-shaped", parallelogram encompasses "substantially parallelogram", and "cigar shape" encompasses "substantially cigar shaped".

Figure 9:
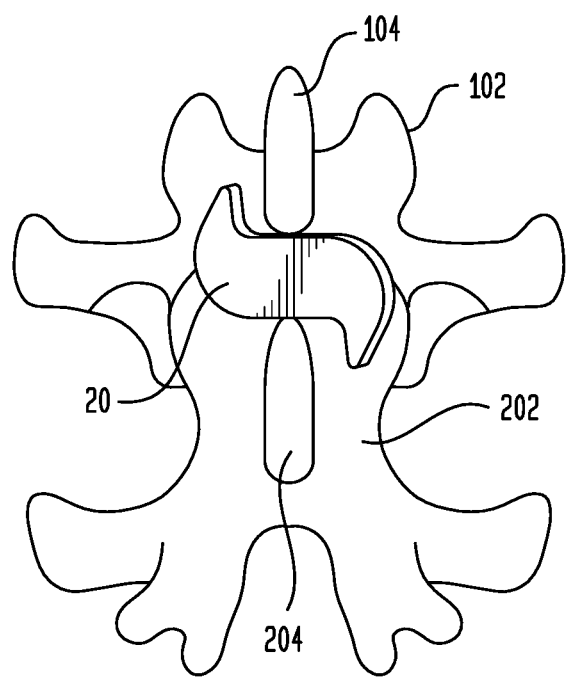
FIG. 9 is a posterior view of an embodiment of an interspinous implant in a partially expanded state situated between two spinous processes.
Figure 10:
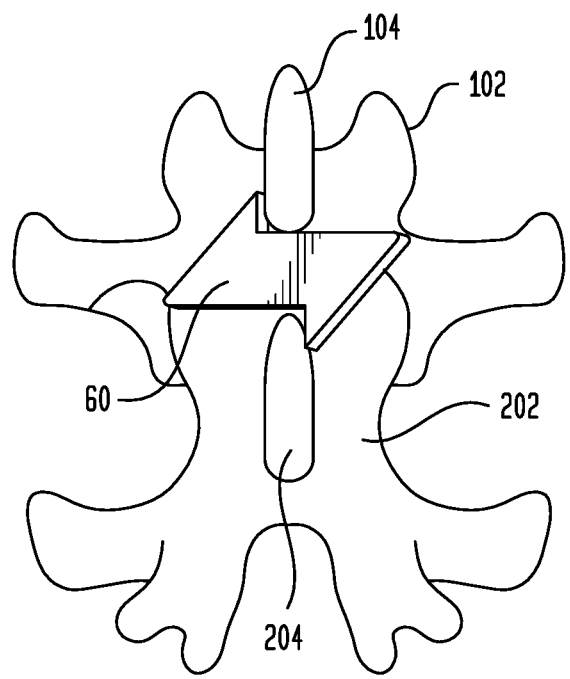
FIG. 10 is a posterior view of an embodiment of an interspinous implant in an expanded Z-shape state situated between two spinous processes.
Figure 11:
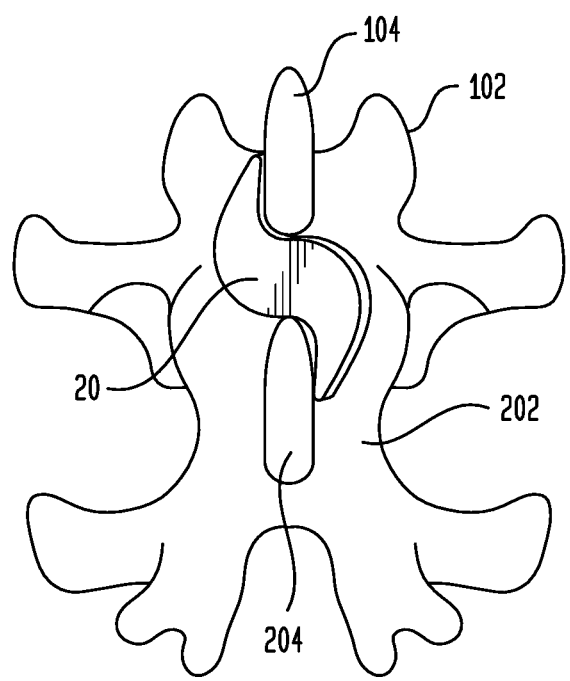
FIG. 11 is a posterior view of an embodiment of an interspinous implant in an expanded S-shape state situated between two spinous processes.

A swellable, resilient self-retaining interspinous implant in accordance with the present disclosure provides a unique support for the interspinous space by virtue of the ability of the fluid absorbing polymeric medium described herein to swell and deswell based on load. The indwelling implant absorbs fluid and expands in the interspinous space until it becomes constrained by the walls of the space. The hydrophilic nature of the implant causes the implant to imbibe fluid and exert positive pressure against the oppositely disposed spinous processes of the adjacent vertebrae, thus maintaining a certain degree of distraction. See, e.g., FIGS. 9-11. During flexion, the implant absorbs fluid and expands, e.g., the centrally disposed cross body, to maintain contact with the superior and inferior faces of the spinous processes as they separate. During extension, the expanded implant exerts mild, yet sufficient force to retard extension when an extension load is applied. In embodiments, the implant does not distort under such loads since fluid is expressed from the implant, thereby allowing the relative volume and mass of the implant to decrease without loss of form. In embodiments, the curvilinear cross body illustrated, e.g., in FIG. 1 functions as a shock absorber having a spring function when, e.g., it flattens from pressure applied by the superior and inferior spinous processes. In addition, as pressure is exerted on the curvilinear cross body, it flattens, thus causing the respective retaining ends to be pushed against the respective outer sagittal faces of the superior and inferior processes, increasing the anchoring force applied by the retaining members.

In embodiments, a polymer configuration includes two polymer phases of different hydrophilicity, the less hydrophilic phase having higher content of hydrophobic groups and more hydrophilic phase having higher content of hydrophilic groups. The less hydrophilic phase is preferably crystalline and more hydrophilic phase is preferably amorphous, as can be established from X-ray diffraction.

In embodiments, hydrophobic groups are pendant nitrile substituents in 1,3 positions on a polymethylene backbone, such as poly(acrylonitrile) or poly(methacrylonitrile). The hydrophilic phase may contain a high concentration of ionic groups. In embodiments, hydrophilic groups are derivatives of acrylic acid and/or methacrylic acid including salts, acrylamidine, N-substituted acrylamidine, acrylamide and N-substituted acryl amide, as well as various combinations thereof. In embodiments, a combination contains approximately two thirds acrylic acid and its salts (on molar basis), the rest being a combination of plain and N-substituted acrylamides and acrylamidines.

In embodiments, at least one polymeric component is a multiblock copolymer with alternating sequences of hydrophilic and hydrophobic groups. Such sequences are usually capable of separating into two polymer phases and form strong physically crosslinked hydrogels. Such multiblock copolymers can be, for example, products of hydrolysis or aminolysis of polyacrylonitrile or polymethacrylonitrile and copolymers thereof. For convenience, polymers and copolymers having at least about 80 molar % of acrylonitrile and/or methacrylonitrile units in their composition may be referred to as "PAN". Hydrolysis and aminolysis of PAN and products thereof are described, for example, in U.S. Pat. Nos. 4,107,121; 4,331,783; 4,337,327; 4,369,294; 4,370,451; 4,379,874; 4,420,589; 4,943,618, and 5,252,692, each being incorporated herein by reference in their respective entireties.

In embodiments, a fluid absorbing polymer for the interspinous implant is a synthetic composite of a cellular (or domain) type with continuous phase formed by a hydrophobic polymer or a hydrophilic polymer with low to medium water content forming a "closed cell" spongy structure that provides a composite with good strength and shape stability. Examples of suitable polymers are polyurethanes, polyureas, PAN, and highly crystalline multiblock acrylic and methacrylic copolymers. The polymer should be sufficiently permeable to water. In embodiments, the continuous phase is formed by a strong hydrophilic polymer with sufficient permeability for water but impermeable to high-molecular solutes. Examples of such polymers are highly crystalline hydrogels based on segmented polyurethanes, polyvinylalcohol or multiblock acrylonitrile copolymers with derivatives of acrylic acid. In embodiments, suitable polymers for the continuous phase in cellular composites have a water content in fully hydrated state between about 60% by weight and about 90% by weight, e.g., between about 65% and about 85% by weight, e.g., about 60% to 70% by weight.

The second component of the fluid absorbing polymer may be a highly hydrophilic polymer of high enough molecular weight to prevent permeation of the hydrophilic polymer through the continuous phase. This component is contained inside the matrix of the continuous phase. The entrapped hydrophilic polymers (the so-called "soft block") may be high-molecular weight water-soluble polymers, associative water-soluble polymers or highly swellable hydrogels containing, in a fully hydrated state, an amount of hydration which is, in embodiments, at least about 5% greater than the hydrophobic component. For example, the second component hydrated to at least about 65% when the first component is hydrated to about 60%. In embodiments, e.g., from the second component could be fully hydrated at from about 95% of water and up to about 99.8% of water. Such hydrogels are very weak mechanically. However, it may not matter in composites where such polymers' role is generation of osmotic pressure rather than load-bearing, with e.g., compression strength in full hydration in the range of about 0.01 $MN/m^2$ or lower.

A system with closed cells (or domains) containing highly swellable or water-soluble polymers can form composites with very high swelling pressure as needed for the interspinous implant function. Examples of suitable hydrophilic polymers are high-molecular weight polyacrylamide, polyacrylic acid, polyvinylpyrrolidone, polyethyleneoxide, copolymers of ethyleneoxide and propyleneoxide or hyaluronic acid; covalently crosslinked hydrogels such as hydrophilic esters or amides of polyacrylic or polymethacrylic acids; and physically crosslinked hydrogels, such as hydrolyzates or aminolysates of PAN.

In embodiments, associative water-soluble polymers capable of forming very highly viscous solutions or even soft physical gels are utilized. For example, associative polymers containing negatively charged groups, such as carboxylates, sulpho-groups, phosphate groups or sulfate groups. In embodiments, associative polymers are utilized which are formed by hydrolysis and/or aminolysis of PAN to high but finite conversions that leave a certain number of nitrile groups (typically, between about 5 and 50 molar %) unreacted.

In embodiments, fluid absorbing polymer composites have both a continuous phase and a dispersed phase formed by different products of hydrolysis or aminolysis of PAN. In this case, both components are compatible and their hydrophobic blocks can participate in the same crystalline domains. This improves anchorage of the more hydrophilic component and prevents its extraction or disassociation. The size of more hydrophilic domains may vary widely, from nanometers to millimeters, preferably from tens of nanometers to microns.

The ratio between the continuous discrete phase (i.e., between more hydrophobic and more hydrophilic components may vary from about 1:1 to about 1:100 on a dry weight basis, e.g., a ratio ranging from about 1:2 to about 1:20. Examples of compositions and implants are described in U.S. Pat. Nos. 6,264,695 and 6,726,721, both of which are incorporated herein by reference in their entireties. An example of a method of making a fluid absorbing polymer composite is described in U.S. Pat. No. 6,232,406, herein incorporated by reference in its entirety.

Examples of suitable hydrogel forming copolymers are prepared by a partial alkaline hydrolysis of polyacrylonitrile ("HPAN") in the presence of sodium thiocyanate (NaSCN). The resulting hydrolysis product is a multi-block acrylic copolymer, containing alternating hydrophilic and hydrophobic blocks. Hydrophilic blocks contain acrylic acid, acrylamidine, and acrylamide. In embodiments, for example, a PAN hydrolysate polymer (referred to herein HPAN I) (46±1% conversion of hydrolysis) having the following composition: acrylonitrile units ~53-55%, acrylic acid units ~22-24%, acrylamide units ~17-19%, acrylamidine units ~4-6%, as determined by $^{13}C$ NMR, is dissolved in a suitable solvent such as a ~55% solution of sodium thiocyanate in water to form a viscous solution. The viscous solution is poured into a porous mold having, e.g., a cavity dimensioned and configured to approximate at least a portion of the space between two spinous processes of two adjacent vertebrae, the cavity defining first and second end portions and a center portion connecting the first and second end portions. The solution can then be solvent cast, e.g., by solvent exchange (e.g., water for NaSCN). The pores should be sufficiently small as to not permit the polymer to diffuse or leak out of the mold. In another form, the hydrogel used to make the interspinous implant is obtained by reacting an aquagel of PAN, formed by dissolving the polymer in an aqueous solvating solution such as high concentration of sodium thiocyanate. The resultant solution of PAN is thereupon coagulated through addition of a suitable aqueous solvent or water miscible solvent. The coagulum is further reacted in a hydrolyzing basic or acidic medium. The PAN aquagel can then be processed as a thermoplastic and molded to obtain the desired shape. These methods are described in U.S. Pat. No. 4,943,618.

A more rigid fluid absorbing polymer may be another PAN hydrosylate polymer, referred to herein as HPAN II (28±1% conversion of hydrolysis), having the following composition: acrylonitrile units ~71-73%, acrylic acid units ~13-15%, acrylamide units ~10-12%, acrylamidine units ~2-4%, as determined by $^{13}$C NMR, dissolved in ~55% NaSCN which can be solvent cast, washed, dried and cut to a suitable shape.

The interspinous implant optionally includes an interiorly embedded support member. The support member occupies at least a portion of the interior of the implant. The support member is preferably in the form of a fabric or a foil, but may also be a series of individual fibers or ribbons which are arranged in parallel or non-parallel fashion. The fabric may be woven or non-woven and may be in the form of a mesh. The size of interstices in the mesh is not deemed critical and it is contemplated that various mesh sizes are suitable. A fabric support member may be made of a polymeric material which is natural, e.g., cotton, or synthetic, e.g., polyester, polyamide, or other materials such as metal fiber, fiber glass, and carbon fiber. Methods of making fabric from these materials and others are well-known to those skilled in the art. Foils herein may also be made of metal or polymeric material and are well-known. Thus, the support member may be constructed from relatively durable materials including, but not limited to, metal foil, plastic foil, metal fibers, polymeric fibers of materials such as polycarbonate, polyethylene, polypropylene, polystyrene, polyethylene terephthalate, polyamide, polyurethane, polyurea, polysulfone, polyvinyl chloride, acrylic and methacrylic polymers, expanded polytetrafluoroethylene (Goretex®), ethylene tetrafluoroethylene, graphite, etc. Polyester mesh made of Dacron® (commercially available from E. I. du Pont de Nemours and Company) or nylon are also suitable. These materials can be used either alone, or in a composite form in combination with elastomers or hydrogels. In embodiments, mesh, woven, non-woven, perforated, or porous formats of these materials which will allow solid anchoring in the implant are utilized. Alternatively, the support member may be exteriorly disposed, e.g., a jacket which surrounds all or part of the interspinous implant.

In embodiments, the support member may be an interiorly disposed braided three-dimensional construct which utilizes unique capabilities manifest by three-dimensional braid architecture. Three-dimensional braiding techniques allow construction of fiber architectures with a high degree of structural integrity and fiber volume fractions, a wide range of pore geometries and pore distribution, and the unique ability to maintain and/or to selectively limit the outer dimensional configuration of the implant while providing a convenient modality for dimensional compression into a desirable implantation configuration. The braided three-dimensional support member is anchored in the implant and provides reinforcement to the implant which increases structural integrity, creep resistance and assists in preventing bulging of the implant under load bearing conditions.

Fibers or strips useful for forming the three dimensional braided support member may be monofilament or multifilament or combinations of the two. Although the term "fiber" generally refers to a flexible, slender, elongated, threadlike object or structure of ellipsoid cross-section, for convenience, "fiber" as used herein also encompasses a "strip", i.e., material which can be elongate and flat. Suitable materials and techniques for forming monofilament of multifilament fibers such as yarn or rovings are well-known to those skilled in the art. For example, suitable fiber forming materials include polyamide, polyethylene terephthalate, polypropylene, polyethylene, PEEK, carbon, ceramic, glass and combinations thereof. Three-dimensional braiding techniques are also well-known to those skilled in the art. See, e.g., Ko, Ceramic Bulletin, Vol. 68, No. 2, pp. 401-414 (1989). Advantageously, the fibers in a braid interlace at angles greater than zero, but less than ninety degrees. The orientation of the fibers or strips in a braid allows for three-dimensional malleability in a three-dimensional fiber architecture. In addition, the void to fiber ratio is adjustable, i.e., the architecture can be made more or less dense depending on the braiding angle and/or geometry of yarn/roving cross-section. The void to fiber ratio can range from about 0.3 to about 3.0.

Three-dimensional braiding techniques provide the ability to assume complex structural shapes. By utilizing an advantageous zigzag path within a three-dimensional architecture, the fibers are capable of shortening their length along defined dimensions and to elongate as well, until a desired jamming configuration is achieved. In embodiments, the support member is configured and dimensioned to correspond to the shape of the void in the interspinous cavity. Accordingly, the support member may be configured in the shape of a 2 or 3 dimensional S-shape or Z-shape. In embodiments, the support member can have a shape which does not correspond to the exterior shape of the interspinous implant. Concave or convex structures are also contemplated. In embodiments, the three-dimensional support member may be configured into other geometric shapes such as rectangular, conical, frusto-conical or pyramidal. Irregular shapes may also be utilized. The support member may be hollow or filled with braided fiber. In addition, a braided support member may be engineered to be particularly conducive to anisotropic expansion and/or contraction, thus permitting a highly optimized delivery shape. Thus, the braided support member can be made to expand or be stretched along one axis while remaining relatively fixed along another axis. Such anisotropic expansion and contraction may be utilized to enhance preferential swelling of the interspinous implant in predetermined dimensions. In this manner, the support member enhances the ability of the interspinous implant to exert positive pressure against the vertebral processes. Inherent anisotropic contraction may be facilitated by exerting sufficient pressure against the engineered contractile axis, thus allowing the braided support member to be selectively manipulated into a desired implantation shape of reduced and optimized cross-section.

In embodiments, the support member includes a portion that is interiorly disposed and an exteriorly disposed portion which extends out of the body of the implant. The exteriorly disposed portion may be utilized to anchor the implant to surrounding tissue or bone. The exteriorly disposed portion of the support member may be, e.g., oblong, tail shaped and the like, and is adapted and configured to wrap around bone and/or surrounding tissue such as the interspinous ligament.

In embodiments, an interspinous implant optionally includes one or more wear reducing surfaces to prevent contact points between the implant and bone from degrading the implant and/or the bone. The wear reducing surface can be a clearly defined separate layer such as a sheath or patch, or it can be an integral layer which has no clearly defined boundary between the material which makes up the body of the implant and the wear reducing surface. The interconnecting cross body of the implant may be subject to a great deal of wear during extension and flexion as it rubs against the opposing vertebral bony surfaces, e.g., the spinous processes. The wear reducing surface serves to protect the interiorly disposed cushiony material which makes up the body of the central portion of the implant and provides a smooth, durable contact surface which reduces friction and consequent wear of the implant and/or bone. In embodiments, a tubular sheath surrounds the cross body of the implant which acts as a wear reducing surface. In embodiments, a wear reducing patch may be applied to the implant at desired locations where it is determined that frictional engagement is unwarranted. The sheath or patch should be flexible to conform to the changing dimensions of the implant which are contemplated herein. In embodiments, the sheath or patch may be made of a non-porous material which is fashioned from a sheet which, in the case of a tubular structure has two ends which are joined by an adhesive, a hot melt process or any other suitable method known by those skilled in the art. A seamless tubular sheath may be extruded or drawn from suitable materials to form a tube. Suitable materials include olefins such as polyethylene, polyporopylene, and polymers such as PTFE, polyamide, polyethylene terephthalate, silicone and PEEK.

The sheath or patch may also be constructed from woven, non-woven, knit and braided fibers such as those described above in connection with the interiorly embedded support member. A patch or sheath may also be constructed from a porous material which can include membranes made of the above materials or from fibers made of the above materials oriented to provide suitable institial spaces. The sheath or patch may be applied to the implant with or without adhesives. Suitable adhesives are well-known in the art. If applied to the central portion of the implant, a sheath may be held in place by the oppositely disposed end retainer portions without need of an adhesive.

In embodiments, the implant may be constructed such that a layer of durable wear reducing material is integrally formed into the implant. For example, a layer of HPAN II or silicone can be made to surround a softer layer of HPAN I in the central portion of the implant. In the case of HPAN I and II, as described below, the two polymers can be allowed to intermingle and create a smooth transitional boundary between the two polymers.

In embodiments, an interspinous implant may be manufactured by providing a mold having, e.g., two corresponding halves. One half is secured to the other half and filled with a liquid swellable polymer such as a fluid absorbing polymer. The polymer is cured or fixed, e.g., by solvent casting, ionic gelation, photo-polymerization and the like. In the case of solvent casting, the mold may be made of material which is impermeable to the fluid absorbing polymer but permeable to water. The mold is placed in a water bath to extract the solvent (e.g., sodium thiocyanate) which causes the polymer to coagulate. The mold may then be opened and any remaining solvent in the interspinous implant is extracted. After curing, the interspinous implant is removed.

In embodiments, a solution of HPAN that will have a swollen water content of 20% polymer 80% water is injected using a 12 gage needle into an isotropic percutaneous implant porous polymeric mold composed of, e.g., Porex™, Lexan™, polycarbonate, combinations of polyimide and polyurethane or other materials known to those skilled in the art. Upon filling of the mold, the mold is transferred into a large volume of purified water and the implant is extracted until all residual salts and other soluble contaminants are removed from the implant. In embodiments, the implant is removed from the mold, packaged in Tyvek™, substantially dehydrated and then sterilized by placing in an autoclave.

The implant can be dried using compressive fixtures to impart an anisotropically dried configuration In embodiments, an interspinous implant may be manufactured by providing a support member such as a suitably shaped mesh or a three-dimensional braided support member of desired configuration and placing it in a mold. A fluid absorbing liquid polymer is added to the mold and infuses into the interstices of the support member until the support member is preferably saturated. In embodiments, a gap, e.g., about 1 mm, is left between one or more sides of the support member and the walls of the mold. Fluid absorbing liquid polymer is allowed to fill the gap between the mold and the support member. As the support member absorbs fluid absorbing liquid polymer additional amounts of the fluid absorbing liquid polymer can be added. When the fluid absorbing polymer is cured or fixed, e.g., by solvent casting, ionic gelation, photo-polymerization and the like, it solidifies and creates a continuous matrix throughout the support member and also forms a layer surrounding and encapsulating the support member. In the case of solvent casting, the mold may be made of material which is impermeable to the fluid absorbing polymer but permeable to water. The mold is placed in a water bath to extract the solvent (e.g., sodium thiocyanate) which causes the polymer to coagulate. The mold may then be opened and any remaining solvent in the interspinous implant is extracted. If it is desired to leave one or more sides of the interspinous implant open to the support member, then the desired side(s) of the support member is placed up against the wall of the mold to prevent formation of a gap for the liquid fluid absorbing polymer to fill.

In embodiments, the fluid absorbing polymer is made to achieve a strong physical bond to the fibers of the support member by incorporating an initial treatment of the fibers of the member, either before or after the weaving or braiding process, with a relatively hydrophobic fluid absorbing polymer to create an encapsulating layer of the relatively hydrophobic fluid absorbing polymer. For example, a hydrogel such as HPAN II may be applied to the fibers as a 10% solution by weight in a solvent (sodium thiocyanate 55% by weight in water) and then coagulated onto the fibers by solvent exchange with an aqueous solution such as water. As the polymer coagulates, it will shrink volumetrically around the fibers, causing a tight physical bond to the fibers. If desired, the treated support member may be placed in a mold and a relatively more hydrophilic fluid absorbing polymer in the liquid state added to create a cohesive continuous polymer matrix which surrounds the support member. For example, a 10% by weight HPAN I in a 55% by weight sodium thiocyanate solution, may be added to the mold. The solvent from the HPAN I solution will cause the outermost surface of the coagulated HPAN II layer surrounding the braided fibers to dissolve and allow commingling of the HPAN I and HPAN II hydrogel polymers at the surface interface which forms a strong adhesive bond when the HPAN I and commingled hydrogels are coagulated by solvent exchange. It should be understood that the support member is optional and that a mold may be filled without such a support member It is contemplated that regions of more or less modulus of elasticity and durability may be incorporated into the interspinous implant. For example, it may be desirable to place a relatively more rigid fluid absorbing polymer at the top and bottom of the interspinous implant, e.g., the portions which contact the vertebral bone. As discussed above, a wear reducing surface may be advantageous, e.g., such as in the central portion of the implant. Accordingly, a liquid fluid absorbing polymer such as HPAN II can initially be added to the mold to create a first layer, followed by placement of the optional support member into the liquid polymer such that the polymer covers and is absorbed into the bottom, e.g., one-third of the reinforcement member. Increasing air pressure can speed the process of saturation of the implant. After a sufficient amount of liquid polymer is absorbed, it can be cured or fixed. If a softer layer of fluid absorbing polymer is desired in the center section of the interspinous implant, a hydrogel such as HPAN I can be added over the bottom layer to fill the mold to, e.g., ⅔ capacity. After the HPAN I is absorbed sufficiently into the reinforcement member, it can be cured or fixed to create a relatively soft middle layer. A third, more rigid layer can then be created by filling the rest of the mold with, e.g., HPAN II and curing or fixing it by solvent casting. It should be understood that any number of layers of varying or the same thickness may created in this fashion. In addition, different fluid absorbing polymers can be used to create zones with different properties. If desired, an adhesive can be added between adjacent layers to insure bonding or, e.g., in the case of the HPAN polymers, the layers can be made to naturally adhere to one another. In embodiments, one or more layers of liquid fluid absorbing polymer can be placed on top of other liquid layers of fluid absorbing polymer and then cured. Differences in density keep the layers from completely intermixing. Some co-mingling of liquid fluid absorbing polymers at layer interfaces can provide for an advantageous smooth transition between layers and reduce or eliminate the need for an adhesive between layers.

In embodiments, one or more tethers such as a string, suture, etc., are incorporated into the interspinous implant. The tether may be utilized in positioning or maintaining the position of the interspinous implant, or its components, during manufacture in molds, and after manufacture as a device for positioning the interspinous implant within an interspinous space. The tether may be simply placed in a central location within the hollow cavity of a support member prior to filling with a liquid fluid absorbing polymer and is then present when the cavity is filled. Alternatively, a tether may be incorporated into the center of a mold when a liquid fluid absorbing polymer insert is coagulated. Alternatively, the tether may be attached directly to the support member at either an interior location or an exterior location if the support member extends out of the fluid absorbing body of the implant.

In embodiments, the interspinous implant includes an internal conduit which is made by placing a tube of predetermined diameter in the mold and then filling the mold with liquid polymer. After coagulation, the tube is removed from the implant leaving a hollow conduit. In embodiments, the conduit is coaxial with the longitudinal axis of the implant and dimensioned to receive a guide wire. See FIG. 7. In embodiments, the tube is pushed through the center of a three dimensional-braid support member and the combination is placed in the mold. Liquid polymer is then added to the mold and allowed to infuse into the interstices of the support member. The mold is the filled with the liquid polymer which is then coagulated. The tube is then removed to leave a conduit for receiving a guide wire.

In embodiments, upon completion of the solvent exchange extraction process the interspinous implants may be hydrated to their fullest extent (~90% equilibrium water content (EWC)). In this fully hydrated state the interspinous implant is readily deformed under modest loads and the hydrogel, e.g., HPAN I or HPAN II, glass transition temperature ($T_g$) is well below room temperature. This is the "relaxed" state of the interspinous implant, the state to which it will return after loading below the critical level. The critical level is the point at which permanent deformation occurs and is further discussed below. In order to provide a reduced configuration (also referred to herein as the first configuration), the interspinous implant may be allowed to dehydrate and enter the xerogel state. A considerable amount of the implant's volume is lost when in the xerogel state as compared to the hydrated state. Advantageously, the fully hydrated interspinous implant may be deformed into a desirable insertion shape and the temperature of the interspinous implant is lowered below its $T_g$ (near freezing point of water). Such an interspinous implant is in a state of "frozen deformation" and it would retain that deformed shape indefinitely. Once the interspinous implant is warmed above its $T_g$, however, the interspinous implant would recover to its original memorized configuration.

The $T_g$ of the hydrogel increases with decreasing water content. This characteristic is exploited by simultaneously raising the $T_g$ while deforming the interspinous implant into a desired shape. In other words, as the interspinous implant dehydrates it is freezing the position of the polymer chains. To regain the original shape of the interspinous implant, the $T_g$ may be lowered by hydration.

In order to obtain Z-shape, parallelogram or cigar shape from, e.g., an S-shaped interspinous implant, reduction in volume deformation is advantageously maintained substantially parallel with the longitudinal axis, e.g. line A-A. In embodiments, the implant can be dried using compressive fixtures to impart an anisotropically dried configuration. In embodiments, this may be accomplished by placing the implant within a collapsible member for exerting compression on the interspinous implant contained within the member. Suitable collapsible members include, e.g., a collapsible sleeve having a rectangular cross-section, a collapsible Z-shaped sleeve, a collapsible parallelogram shaped sleeve, a collapsible cigar shaped sleeve. In embodiments, the collapsible member can be divided into sections that slide over one another to provide a reduction in perimeter dimensions. In embodiments, the collapsible member is porous or semipermeable so that water, either as liquid or as vapor, passes through the member. The collapsible member may be made of an elastic material such as rubber or neoprene fabric which has been made porous by any technique known to those skilled in the art, or a woven or non-woven mesh or braid. The collapsible member may also be made of a metal having sufficient porosity to allow water to exit from the implant. The collapsible member does, however, need to be stiff enough to be able to exert sufficient compressive force when tension is applied to compress the interspinous implant, i.e., it should not be so elastic that it deforms without being able to exert sufficient compressive force.

In operation, the collapsible member exerts compression on the interspinous implant. In embodiments, the porous nature of the collapsible member allows water from the implant to escape into the surrounding environment so that the interspinous implant can become dehydrated.

By varying the tension on the collapsible member, the length of the interspinous implant can be extended, thereby decreasing the minor axis and height. This can also be controlled, to some extent, by the speed of dehydration (temperature, pressure and humidity), with longer dehydration time producing longer interspinous implant length and vice versa. In embodiments, one portion of the collapsible member is made to collapse further than other portions to define portions which are relatively more compressed than others.

There are two concerns with respect to drying time and collapsible member tension that should be considered. The first is creep, which may set in if the dehydration time is extended unreasonably long (over several days). The second is permanent deformation which may occur if excessive stress is applied to the implant. Both of these concerns only occur at critical point extremes which are to be avoided. Permanent deformation may occur in the hydrogel implant if the soft-block domains of the polymer are displaced to a point where they cannot reorient themselves into the original lattice configuration, i.e., the memorized shape. This can happen, e.g., by either deforming the original shape so severely that many of the bonds which hold the soft-blocks in place are severed, or by heating the implant sufficiently above the $T_g$ to cause the soft-block domains to permanently or irrevocably assume a new configuration outside of the originally contemplated structure, which causes an undesirable change in shape. Thus, the melting point of the soft block should not be exceeded. The melting point of the soft block may vary based on the amount of water content. Such melting points may be determined by conventional techniques known to those skilled in the art. For example, at 18% hydration of HPAN I, permanent deformation is manifest at temperatures over 105° C.

In embodiments, the majority of the dehydration process can occur at room temperature over an extended period of time (e.g., 18 to 36 hours). The interspinous implant can be monitored to determine the extent of dehydration and the time period adjusted accordingly. Relative humidity, air circulation, air pressure and room temperature should be controlled during this period. In embodiments, conditions are about 21° C. at 50% relative humidity under moderate airflow. Once the interspinous implant has reached <~30% water content it may be forced dry at elevated temperature, e.g., from about 25° C. to about 105° C. for typically less than about 24 hours to rapidly remove remaining water. As above, the state of dehydration may be monitored to determine if greater or lesser amounts of time are needed. When the interspinous implant is substantially dehydrated, the implant is fairly rigid in its state of frozen deformation. Alternatively, a slight degree of hydration provides some flexibility to the implant. The less dehydrated, the more flexible. It is contemplated herein that "substantially dehydrated" preferably encompasses from about 12% or less, to about 30% water by weight of the implant, e.g., about 3% to about 30%, about 5% to about 25%, about 10% to about 15%, about 15% to about 30%, about 20 to about 25% by weight.

Upon completion of forced dehydration, the interspinous implant is extremely stable in terms of shelf life, providing that it is kept dry. Even brief exposure to humidity during the sterilization process should not have significant effects. Temperatures above about 80° C. should be avoided for extended periods as this may bring the implant above its $T_g$ if it has absorbed some small amount of water vapor.

Surface irregularities may be present on a dehydrated compressed implant which was compressed as described above by a collapsible member by virtue, e.g., of some extrusion of the hydrogel through pores or through interstitial spaces of the member. For example, a woven or nonwoven collapsible sleeve may have interstitial spaces that allow hydrogel to extrude therein under compressive force. In addition, after compression, as described above, the dimensions of the implant may be different than the ultimate dimensions desired by the practitioner. Both of these instances can be remedied by post-compression thermoforming of the interspinous implant. In this aspect, a dehydrated, compressed interspinous implant is placed within a mold which may be advantageously pre-heated to about 70-150° C., but more preferably, closer to the melting point of the polymer, e.g., about 105° C. Care should be taken to avoid subjecting the interspinous implant to excess heat which causes the hydrogel to exceed its critical point, and thus causing permanent deformation of the interspinous implant. If the temperature is high, the interspinous implant must be quickly removed from the mold to avoid permanent deformation. The mold is machined to the exact desired final dimensions of the xerogel interspinous implant and essentially irons out surface roughness to a substantially smooth surface, which is less abrasive to surrounding tissue when implanted. If desired, and if the dehydrated implant is compressed by a compressive member or by gas compression, but has not achieved, e.g., an ideal enough configuration, or if the ends are not sufficiently blunted or otherwise tapered, post-compression thermoforming may be utilized to fine tune the shape as well as remove any surface irregularities which may be present.

An interspinous implant according to the disclosure herein may contain a medicinal agent. "Medicinal agent" is used in its broadest sense and it includes any substance or mixture of substances which may have any clinical use. It is to be understood that medicinal agent encompasses any drug, including hormones, antibodies, therapeutic peptides, etc., or a diagnostic agent such as a releasable dye which has no biological activity per se. Thus, in its broadest aspect, a method of delivery herein may be defined as the release of any substance for clinical use, which may or may not exhibit biological activity.

Examples of medicinal agents that can be used include anticancer agents, analgesics, anesthetics, anti-inflammatory agents, growth factors such as BMPs, antimicrobials, and radiopaque materials. Such medicinal agents are well-known to those skilled in the art. The medicinal agents may be in the form of dry substance in aqueous solution, in alcoholic solution or particles, microcrystals, microspheres or liposomes. An extensive recitation of various medicinal agents is disclosed in Goodman and Gilman, The Pharmacological Basis of Therapeutics, 10th ed. 2001, or Remington, The Science and Practice of Pharmacy, 21 ed. (2005). As used herein, the term "antimicrobial" is meant to encompass any pharmaceutically acceptable agent which is substantially toxic to a pathogen. Accordingly, "antimicrobial" includes antiseptics, antibacterials, antibiotics, antivirals, antifungals and the like. Radiopaque materials include releasable and non-releasable agents which render the interspinous implant visible in any known imaging technique such as X-ray radiographs, magnetic resonance imaging, computer assisted tomography and the like. A radiopaque material may be located throughout the implant or in specific locations, e.g., the cross body. The radiopaque material may be any conventional radiopaque material known in the art for allowing radiographic visualization of an implant, and may be, e.g., metal wire or flakes made from a biocompatible material, such as titanium, tantalum, stainless steel, or nitinol; or metallic salts (such as barium compounds).

In embodiments, a radiopaque material is incorporated into a portion of at least one retaining member of an interspinous implant. In embodiments, both retaining members contain a radiopaque material. In embodiments, radiopaque material is distributed throughout the retaining member. In embodiments, radiopaque material is contained in one or more portions of a retaining member. In embodiments, one or both retaining members have an end portion, e.g., the tips, or an edge, which contains the radiopaque material. In embodiments, upon expansion of the implant from the first configuration to the second configuration, end portion(s) which contain the radiopaque material define a first position while in the first configuration. As the implant expands to the second configuration, the retaining member, e.g., compacted configuration in FIG. 8, retaining member 32 and/or 34 moves relative to the spinal processes, e.g., partially expanding as shown in, e.g., FIG. 9. In this manner, the position of the expanding implant can be readily ascertained using radiographic techniques. Any positional adjustments to the implant can be made as a result using minimally invasive techniques. As the implant continues to expand, reaching its expanded second configuration (see, e.g., FIGS. 10 and 11), the radiopaque materials provide a ready indication of the position of the retaining members, thereby allowing practitioners to confirm proper placement of the implant. In addition, visualization of the radiopaque materials allows the fluid levels of the implant to be quantified depending on the position of the retaining members. In embodiments, while expanding from the first configuration to the second configuration, each retaining member defines a distance over, e.g., an arc or a line which can be divided into discrete units. Each unit of distance will correspond to an amount of fluid absorbed by the implant which can be determined in advance as a standardized common property of the implants.

Medicinal agents may be incorporated into the interspinous implant at various points in the manufacturing process. For example, a suitable medicinal agent can be mixed with a fluid absorbing liquid polymer before it is cured or fixed. Alternatively, a suitable medicinal agent may be dissolved into a solvent cast solution and then diffused into the hydrogel in accordance with normal kinetic principles. If the interspinous implant is then dehydrated, the medicinal agent collects in the interstices of the hydrogel and/or the braided three-dimensional reinforcement member.

A substantially dehydrated interspinous implant according to the disclosure herein may be sterilized by any suitable conventional means, e.g., steam, ethylene oxide, irradiation, etc. and packaged for distribution. A kit containing the sterilized interspinous implant and a package insert describing the interspinous implant, along with instructions is useful for medical practitioners.

Techniques for implanting surgical devices in the interspinous space are well-known. In the present case, minimally invasive implantation techniques are improved and facilitated by the reduced dimension and overall configuration of the first configuration. In addition, the ability to provide custom implantation shapes allows an optimal insertion shape to be manufactured. In embodiments, percutaneous delivery of the implant is utilized to deposit the implant into the intervertebral space. In embodiments, utilization of a guide wire delivery system allows percutaneous delivery of the implant and an even smaller incision to be made than is normally used, e.g., in the case of cannulas. For example, a small incision is made proximate to the interspinous space that will receive the implant. The interspinous ligament is then dilated using, e.g., a bent awl. A distractor is used to separate the spinous processes and open the interspinous space for receiving the implant. In embodiments, the implant is then guided into the interspinous space with the guide wire. For example, the implant is pushed across the interspinous space until the inwardly facing portion of the distal end portion of a Z-shape implant contacts an outwardly facing sagittal portion of the spinous process. In embodiments, the proximate end pushes through and acts like a barb to engage the other side of the spinous process. See, e.g., FIG. 8. If a guide wire is used, the guide wire is then removed from the implant. As the implant expands to the second configuration, the internal conduit is optionally compressed and collapses upon itself and the opposing ends of the implant envelope the opposing sides of the spinous processes of the vertebrae to anchor the implant in place as shown, e.g., in FIGS. 10 and 11. In addition, the interspinous space is occupied by the cross body of the implant as described above. In operation, the implant gently distracts the interspinous space by virtue of its ability to swell and be resilient. The polymeric materials and optional support members described herein provide a soft, yet resilient, shock absorbing cushion to maintain a distracted interspinous space. The retaining members gently keep the implant well-supported laterally in the interspinous space. In this manner, reinforcement is provided to damaged and/or healing discal architecture and nerve compression on extension is prevented and alleviated.

The following example is included to illustrate certain features in connection with a swellable interspinous stabilization implant herein. Since it is merely exemplary, the example is not intended to limit any aspect of the disclosure of this specification.

EXAMPLE

Prospective Surgical Insertion of a Swellable Interspinous Implant

A patient is placed into the prone position on a Wilson frame. Fluoroscopic imaging is then used to verify levels of dissection and appropriate visualization of the spinous processes and vertebral bodies. Skin markings using a skin marker are made. The patient's spine is then sterilely prepped and draped. Using a direct posterior approach a small lumbar midline incision is made. A 1.6 mm k-wire is inserted into the opening. Using fluoroscopic imaging, depth and placement are verified. Once correct placement and depth of the guide wire (k-wire) is verified an initial dilator is inserted over the k-wire. Following successful placement of the initial dilator a second dilator is inserted coaxially over the initial dilator to further distract the interspinous space between the vertebrae. If indicated, consecutively larger dilation cannulas are inserted over the initial dilator and second dilator until desired sized dilator is reached. Once the desired distraction has been reached, an insertion cannula is slid over the dilators. Following successful placement of the insertion cannula, the k-wire and all insertion dilators, e.g., are removed. Insertion cannula placement is verified using fluoroscopic imaging. A dehydrated implant in the first configuration and of predetermined size is inserted into the insertion cannula and is pushed into place using an implant insertion device. The implant insertion device includes a handle and an extension rod having an end which removably holds the implant. The insertion cannula and implant insertion device are removed, leaving the dehydrated implant in the interspinous space. Fluoroscopic imaging is used to verify position of the implant. The implant and surrounding tissue are irrigated using normal saline solution and periodically thereafter for ten minutes to allow the implant to begin swelling. The patient is closed using established closing procedures. As depicted in FIGS. 8 through 11, the dehydrated implant 30, 30', 40 or 50 swells and fills the interspinous space, reaching its hydrated, working volume, 10, 20 or 60.

It should be understood that the examples and embodiments of the invention provided herein are preferred embodiments. Various modifications may be made to these examples and embodiments without departing from the scope of the invention which is defined by the appended claims. For example, those skilled in the art may envision additional polymers and/or hydrogels which can be compacted and shaped according to the techniques described herein. Similarly, the shapes of the compacted and hydrated or expanded interspinous implant described herein are exemplary and any suitable compacted and/or expanded interspinous implant shape can be subjected to the techniques described herein to create an optimally shaped, substantially dehydrated interspinous implant for minimally invasive insertion into the disc space. Those skilled in the art can envision additional collapsible members for exerting substantially uniform compression on the implant which are not set forth herein. In addition, process parameters such as temperature, humidity, pressure, time and concentration may be varied according to conventional techniques by those skilled in the art to optimize results.

What is claimed is:

1. A swellable, resilient interspinous implant comprising two oppositely disposed retaining members connected by a centrally disposed cross body, the cross body defining a longitudinal axis, each retaining member extending in opposite directions relative to each other and perpendicular to the longitudinal axis, the implant being dimensioned and configured to fit between two spinous processes of two adjacent vertebrae, wherein the implant is made of a fluid absorbing polymer which expands from a substantially dehydrated compact first configuration to an expanded second configuration upon absorption of fluid, the implant extending asymmetrically about the axis when in the expanded configuration.

2. A swellable, resilient interspinous implant according to claim 1, wherein the cross body is dimensioned and configured such that when in the second configuration, the cross body has a volume that is greater than the space between two adjacent superior and inferior spinous processes such that when the spinous processes are in a neutral position the cross body is compressed slightly.

3. A swellable, resilient interspinous implant according to claim 2, wherein the cross body defines a height ranging from about 8 mm to about 16 mm.

4. A swellable, resilient interspinous implant according to claim 1, wherein the compact first configuration defines a Z-shape.

5. A swellable, resilient interspinous implant according to claim 1, wherein the compact first configuration defines a cigar shape or a parallelogram shape.

6. A swellable, resilient interspinous implant according to claim 1, wherein the implant defines an S-shape.

7. A swellable, resilient interspinous implant according to claim 1, wherein the cross body has a flat superior surface dimensioned and configured to receive a superior process of a superior vertebrae.

8. A swellable, resilient interspinous implant according to claim 7, wherein the flat superior surface defines a width perpendicular to the longitudinal axis which ranges from about 8 mm to about 15 mm.

9. A swellable, resilient interspinous implant according to claim 7, wherein the flat superior surface defines a length along the longitudinal axis which ranges from about 10 mm to about 15 mm.

10. A swellable, resilient interspinous implant according to claim 1, wherein at least one of the retaining members contains a collapsible aperture which is transverse of the longitudinal axis.

11. A swellable, resilient interspinous implant according to claim 10, wherein the collapsible aperture is triangular when not collapsed and crescent-shaped when collapsed.

12. A swellable, resilient interspinous implant according to claim 1, wherein the fluid absorbing polymer has a fluid content below about 70% by weight when in the second configuration.

13. A swellable, resilient interspinous implant according to claim 1, further comprising an interiorly disposed support member and a tether for securing the implant to bone or tissue.

14. A swellable, resilient interspinous implant according to claim 13, wherein the support member extends out of the fluid absorbing polymer.

15. A swellable, resilient interspinous implant according to claim 1, further comprising an internal conduit.

16. A swellable, resilient interspinous implant according to claim 1, further comprising a tether attached to the implant for securing the implant to bone or tissue.

17. A swellable, resilient interspinous implant according to claim 1, wherein the fluid absorbing polymer is a hydrogel.

18. A swellable, resilient interspinous implant according to claim 1, wherein the fluid absorbing polymer contains a plasticizer.

19. A swellable, resilient interspinous implant according to claim 1, further comprising a medicinal agent.

20. A method of manufacturing a swellable, resilient interspinous implant comprising:
providing a mold having a cavity dimensioned and configured to approximate at least a portion of the space between two spinous processes of two adjacent vertebrae, the cavity defining first and second end portions and a center portion connecting the first and second end portions;
providing a liquid fluid absorbing polymer;
filling the mold with the liquid polymer;
solidifying the liquid polymer to form a swellable, resilient interspinous implant according to claim 1; and
dehydrating the implant under compression to form a compacted implant of reduced dimension having a shape memory.

21. A method of treating a degenerative condition of the spine comprising creating an incision and inserting, through the incision, between two spinous processes of two adjacent vertebrae, a swellable resilient interspinous implant in the compact first configuration according to claim 1.

22. A swellable, resilient interspinous implant comprising two oppositely disposed retaining members connected by a centrally disposed cross body, the cross body defining a horizontal axis, each retaining member extending in opposite directions with respect to each other and asymmetrically with respect to the horizontal axis, the implant being dimensioned and configured to fit between two spinous processes of two adjacent vertebrae, wherein the implant is made of a fluid absorbing polymer which expands from a substantially dehydrated compact first configuration to an expanded second configuration upon absorption of fluid, the compact first configuration defining a Z-shape, or a parallelogram shape, the cross body having a rectangular cross-section thereby defining a flat superior surface and a flat inferior surface, at least one retaining member containing a collapsible aperture, and the fluid absorbing polymer having a fluid content below about 70% by weight when in the second configuration and the implant extending asymmetrically about the axis when in the second configuration.

23. A swellable, resilient interspinous implant comprising two oppositely disposed retaining members connected by a centrally disposed cross body, the cross body defining a longitudinal axis, each retaining member extending in opposite directions with respect to each other and asymmetrically with respect to the longitudinal axis, at least a portion of one retaining member containing a radiopaque material, the implant being dimensioned and configured to fit between two spinous processes of two adjacent vertebrae, wherein the implant is made of a fluid absorbing polymer which expands from a substantially dehydrated compact first configuration to an expanded second configuration upon absorption of fluid, the implant extending asymmetrically about the axis when in the second configuration, wherein the retaining member containing the radiopaque material has an end portion which contains the radiopaque material, wherein upon expansion of the implant from the first configuration to the second configuration, the end portion which contains the radiopaque material defines a first position in the first configuration and second positon position in the second configuration, the second position serving as an indication that the implant is in the second configuration.

* * * * *